US009687544B2

(12) United States Patent
Thevenon et al.

(10) Patent No.: US 9,687,544 B2
(45) Date of Patent: Jun. 27, 2017

(54) VETERINARY VACCINE

(75) Inventors: Jerome Thevenon, St-Nazaire-les Eymes (FR); Ferenc Misak, Pilisborosjeno (HU); Miklos Tenk, Budapest (HU)

(73) Assignee: CEVA SANTE ANIMALE, Libourne (FR)

( * ) Notice: Subject to any disclaimer, the term of this patent is extended or adjusted under 35 U.S.C. 154(b) by 28 days.

(21) Appl. No.: 14/383,113

(22) PCT Filed: Mar. 7, 2012

(86) PCT No.: PCT/EP2012/053932
§ 371 (c)(1),
(2), (4) Date: Jan. 27, 2015

(87) PCT Pub. No.: WO2013/131565
PCT Pub. Date: Sep. 12, 2013

(65) Prior Publication Data
US 2015/0174240 A1    Jun. 25, 2015

(51) Int. Cl.
*A61K 39/00*     (2006.01)
*A61K 39/02*     (2006.01)
*A61K 39/108*    (2006.01)
*A61K 39/39*     (2006.01)

(52) U.S. Cl.
CPC .......... *A61K 39/39* (2013.01); *A61K 39/0241* (2013.01); *A61K 2039/521* (2013.01); *A61K 2039/552* (2013.01); *A61K 2039/55566* (2013.01); *A61K 2039/55572* (2013.01); *A61K 2039/55583* (2013.01)

(58) Field of Classification Search
CPC ...................................... A61K 39/39
See application file for complete search history.

(56) References Cited

U.S. PATENT DOCUMENTS 5,554,372 A * 9/1996 Hunter ................ A61K 39/385
424/278.1

FOREIGN PATENT DOCUMENTS

| WO | WO 03/003941 | 1/2003 |
| WO | WO 03/004051 | 1/2003 |
| WO | WO 2004/043286 | 5/2004 |

OTHER PUBLICATIONS

Lo et al (J. Vet. Med. Sci. 71 (7) pp. 897-903, 2009).*
Sheldrake, R. F. et al. "Serum and mucosal antibody responses against *Mycoplasma hyopneumoniae* following intraperitoneal vaccination and challenge of pigs with *M hyopneumoniae*" *Research in Veterinary Science*, Nov. 1, 1993, pp. 371-376, vol. 55, No. 3.
Muneta, Y. et al. "Porcine TLR2 and TLR6: Identification and Their Involvement in *Mycoplasma hyopneumoniae* Infection" *Journal of Interferon & Cytokine Research*, Oct. 2003, pp. 583-590, vol. 23, No. 10.
Martin, M. et al. "Role of Innate Immune Factors in the Adjuvant Activity of Monophosphoryl Lipid A" *Infection and Immunity*, May 2003, pp. 2498-2507, vol. 71, No. 5.
Herbach, N. et al. "Adjuvants designed for *M. hyopneumoniae* vaccines" *International Pig Topics*, Jul. 2005, pp. 7 and 9, vol. 20, No. 5.

* cited by examiner

*Primary Examiner* — Albert Navarro
(74) *Attorney, Agent, or Firm* — Saliwanchik, Lloyd & Eisenschenk

(57) ABSTRACT

The present invention relates to novel compositions for inducing an immune response in mammals. The composition preferably comprises an antigen and a lipopolysaccharide in an oil-in-water formulation. The invention is particularly suited to vaccinate swine against *mycoplasma* infections.

15 Claims, 2 Drawing Sheets

VETERINARY VACCINE

CROSS-REFERENCE TO RELATED APPLICATIONS

This application is the U.S. national stage application of International Patent Application No. PCT/IB2012/051916, filed Apr. 17, 2012, which claims the benefit of U.S. Provisional Patent Application No. 61/476,346, filed Apr. 18, 2011.

The present invention relates to novel compositions for inducing an immune response in mammals. The invention also relates to methods of vaccination of mammals against pathogens, as well as to methods for protecting mammals against diseases. The invention is based more particularly on particular adjuvant formulations which cause strong and stable immune responses. The invention is particularly suited to vaccinate swine against *mycoplasma* infections.

BACKGROUND OF THE INVENTION

*Mycoplasma hyopneumoniae* (Mh) is the etiologic agent of swine enzootic pneumonia. It is one of the most important diseases that affect swine and usually causes the most important loss of animals. The disease generally results in inefficient weight gains and in sickly animals. Mh-infected swine are also subject to secondary infections, eventually leading to death.

Different vaccines for protecting swine against *Mycoplasma hyopneumoniae* infections have been reported. These include, e.g., vaccines comprising surface antigens of Mh (EP283840), a vaccine comprising plasma membranes of Mh, or vaccines comprising live or inactivated Mh bacteria (U.S. Pat. No. 3,917,819, WO2009/61798). The above vaccines, however, do not always provide satisfactory protection in vaccinated swine. In particular, these vaccines do not appear to generate appropriate cellular and humoral responses to cause efficient protection of animals.

Vaccines comprising inactivated Mh strains are also commercially available, such as Respifend®. This vaccine requires several injections.

There is a need for improved compositions inducing better immunogenic responses in animals, to confer stronger protection against diseases caused by pathogenic agents such as Mh.

SUMMARY

The present invention provides compositions and methods that elicit an effective immune response against pathogens in mammals, and can be used to prevent the occurrence and/or reduce the severity of a disease caused by such pathogens, or to correct or improve at least one symptom associated with the disease.

A first object of the invention resides, more specifically, in a composition comprising an antigen and a lipopolysaccharide (LPS) in an oil-in-water formulation. As will be demonstrated, the applicant has discovered that the combination of an LPS and an oil-in-water formulation allows the stimulation of both cellular and humoral immunity, and induces a balanced Th1/2 response which is adapted to efficiently protect mammals against pathogenic diseases.

In a particular embodiment, the composition comprises several antigens, and is efficient to induce an immune response against distinct pathogens.

In a preferred embodiment, at least one antigen is a bacterial antigen, preferably an inactivated bacterium.

A further object of the invention is a vaccine comprising an antigen and a lipopolysaccharide in an oil-in-water formulation.

A further object of the invention is a vaccine comprising a pathogenic antigen and a lipopolysaccharide in an oil-in-water formulation, for use to protect non-human mammals from diseases caused by the pathogen.

The invention also relates to a method for vaccinating a non-human animal against a pathogen, comprising administering to the animal a composition or vaccine comprising a pathogenic antigen and a lipopolysaccharide in an oil-in-water formulation.

The invention further provides a method for inducing or stimulating an antigen-specific humoral and cellular immunity in a non-human animal, comprising administering to the animal a composition or vaccine comprising a bacterial antigen and a lipopolysaccharide in an oil-in-water formulation.

Another object of the invention resides in a method for vaccinating pigs or piglets against *Mycoplasma hyopneumoniae* (Mh), comprising administering to said pigs or piglets a composition or vaccine comprising an inactivated Mh and a lipopolysaccharide in an oil-in-water formulation.

The invention also relates to a method for protecting piglets from diseases caused by Mh infection, comprising administering to the animals a composition or vaccine comprising an inactivated Mh and a lipopolysaccharide in an oil-in-water formulation.

Another object of the invention relates to a method for protecting an animal against a disease caused by *Mycoplasma hyopneumoniae* and/or for reducing the effect of such a disease on said animal, comprising administering to the animal a composition or vaccine comprising an inactivated Mh and a lipopolysaccharide in an oil-in-water formulation.

DETAILED DESCRIPTION OF THE INVENTION

Figure 1:
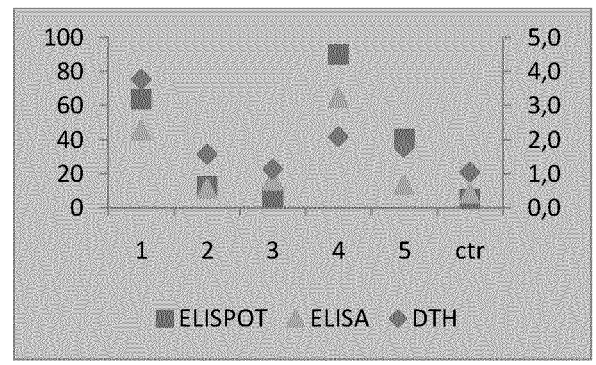
FIG. 1: Humoral and cellular immune response of vaccinated piglets.

The present invention relates to methods and compositions for vaccinating non-human mammals against pathogens. It is particularly suited to protect the animals from diseases caused by said pathogens, or to minimize the severity, duration or symptoms of said diseases. It is suitable to vaccinate any mammals, including pigs, piglets, dogs, cats, horses, cows or veal. It is particularly suited to vaccinate pigs or piglets against *Mycoplasma hyopneumoniae*.

As indicated, the invention provides novel compositions comprising an antigen and a lipopolysaccharide in an oil-in-water formulation. Such compositions surprisingly stimulate both cellular and humoral immunity in treated animals, and induce a balanced Th1/2 response which is adapted to efficiently protect mammals against diseases caused by pathogens. Our results further show a 6-month duration of protective immunity after vaccination with a composition of the invention by a heavy experimental challenge trial using 1 shot of the vaccine at 3 weeks of age in immunized pigs and non-vaccinated controls. The vaccine prevented the body weight loss due to enzootic pneumonia (EP) and significantly decreased the severity of pathological changes caused by *Mycoplasma hyopneumoniae* infection.

The antigen(s) in the composition may be of various natures. In particular, the antigen(s) may be a whole pathogen (e.g., cell, virus) or a portion or extract thereof, such as a membrane, organelle, supernatant, protein or fragment thereof (e.g., a peptide), nucleic acid, lipid, or a combination thereof. The antigen is sometimes referred to as a "pathogenic" antigen since it derived from a pathogen, even if it is not in itself pathogenic.

In a preferred embodiment, the antigen comprises a whole cell or virus, in live, inactivated or killed form. The antigen may also be a recombinant virus comprising an immunogenic epitope.

In a more preferred embodiment, the composition comprises at least one inactivated or killed virus or bacterium, such as one inactivated or killed Mh bacterium. "Inactivated or killed" indicates that the virus or bacterium has lost the ability to cause disease in mammals but retains an immunogenic property thereof, particularly the ability to generate a specific immune response. The term "inactivated bacterium" also includes non-virulent bacteria.

Methods for preparing or selecting inactivated bacteria or viruses are well-known in the art. They include heat-inactivation methods and chemical inactivation methods. Inactivation may be carried out by exposing the bacterium or virus to a chemical agent such as formalin, formaldehyde, paraformaldehyde, β-propiolactone, ethyleneimine, binary ethyleneimine (BEI), thimerosal, or derivatives thereof. Alternatively, inactivation may be carried out by physical treatments such as heat treatment or sonication. Methods of inactivation are well-known to those of skill in the art. The inactivated pathogen may be concentrated by conventional concentration techniques, in particular by ultrafiltration, and/or purified by conventional purification means, in particular using chromatography techniques including but not limited to gel filtration, ultracentrifugation on a sucrose gradient, or selective precipitations, in particular in PEG.

In a typical embodiment, the bacterium is inactivated with ethyleneimine using a final concentration of 500 micrograms/ml. The inactivation is carried out at 37° C. for 24 hours and stopped by adding sodium thiosulfate.

In a preferred embodiment, the composition comprises an amount of antigen sufficient to cause or stimulate an immune response against the pathogen in treated animals. The exact amount required for an immunologically effective dose may vary from subject to subject depending on factors such as the age and general condition of the subject, the nature of the formulation and the mode of administration. The appropriate "effective amount" may be determined by one of ordinary skill in the art using only routine experimentation. For instance, methods are known in the art for determining or titrating suitable dosages of vaccine to find minimal effective dosages based on the weight of the non-human animal subject, concentration of the vaccine and other typical factors. The dosage of the vaccine, concentration of components therein and timing of administering the vaccine which elicit a suitable immune response can be determined by methods such as by antibody titrations of sera, e.g., by ELISA and/or seroneutralization assay analysis and/or by vaccination challenge evaluation.

When the antigen is a whole bacterium (live, inactivated or killed), it is preferably used at a dosage comprised between approximately $10^2$ and $10^{11}$ cells/dose, more preferably from $10^3$ to $10^{11}$ cells/dose. Preferred dosages are comprised between $10^7$ to $10^{10}$ cells/dose.

Also, the compositions may comprise several distinct antigens, particularly 1, 2 or 3, thereby protecting treated animals against different pathogens. In a particular embodiment, the composition comprises at least one antigen derived from at least one of the following pathogenic agents: *Actinobacillus pleuropneumoniae*; Adenovirus; Alphavirus such as Eastern equine encephalomyelitis viruses; *Balantidium coli*; *Bordetella bronchiseptica*; *Brachyspira* spp., preferably *B. hyodysenteriae, B. pilosicoli*, or *B. innocens*; *Brucella suis*, preferably biovars 1, 2 and 3; Classical swine fever virus; African swine fever virus; *Chlamydia* and *Chlamydophila* spp., preferably *C. pecorum* or *C. abortus*; *Clostridium* spp., preferably *Cl. difficile, Cl. perfringens* types A, B and C, *Cl. novyi, Cl. septicum*, or *Cl. tetani*; Digestive and respiratory Coronavirus; *Cryptosporidium parvum*; *Eimeria* spp.; *Eperythrozoon suis*, currently named *Mycoplasma haemosuis*; *Erysipelothrix rhusiopathiae*; *Escherichia coli*; *Haemophilus parasuis*, preferably subtypes 1, 7 and 14; Hemagglutinating encephalomyelitis virus; *Isospora suis*; Japanese Encephalitis virus; *Lawsonia intracellularis*; *Leptospira* spp., preferably *Leptospira interrogans ss lato, Leptospira borgpetersenii, Leptospira inadai, Leptospira meyeri, Leptospira noguchii, Leptospira santarosai, Leptospira weilii*, or *Leptospira wolbachii*, including strains from serogroups or serovars *australis, canicola, grippotyphosa, hardjo, icterohaemorrhagiae, sejroe, Pomona* and *tarassovi*; *Mannheimia haemolytica*; *Mycobacterium* spp., preferably *M. avium, M. intracellulare* or *M. bovis*; *Mycoplasma hyopneumoniae*; Parvovirus; *Pasteurella multocida*; Porcine cytomegolovirus; Porcine parovirus; Porcine reproductive and respiratory syndrome virus; Pseudorabies virus; Rotavirus; Sagiyama virus; *Salmonella* spp., preferably *S. enterica, S. thyphimurium* or *S. choleraesuis*; *Staphylococcus* spp., preferably *S. hyicus*; *Streptococcus* spp., preferably *Strep. suis*; Swine cytomegalovirus; Swine herpes virus; Swine influenza virus; Swine pox virus; *Toxoplasma gondii*; Vesicular stomatitis virus or virus of exanthema of swine; or other isolates and subtypes of porcine circovirus.

In a preferred embodiment, the composition comprises an antigen from at least one of the following pathogens: *Mycoplasma hyopneumoniae*, porcine reproductive and respiratory syndrome virus (PRRS), porcine parvovirus (PPV), *Haemophilus parasuis, Pasteurella multocida, Streptococcus suis, Actinobacillus pleuropneumoniae, Bordetella bronchiseptica, Salmonella choleraesuis, Erysipelothrix rhusiopathiae, leptospira* bacteria, swine influenza virus, *Escherichia coli* antigen, porcine respiratory coronavirus, rotavirus, a pathogen causative of Aujeszky's Disease, and a pathogen causative of Swine Transmissible Gastroenteritis.

In a more preferred embodiment, the composition comprises an inactivated or killed Mh and, optionally, one PCV2 antigen. PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exudative epidermitis, necrotizing lymphadenitis, and congenital tremors. Preferably, a non-human animal subject, such as a pig, is protected to the extent that one to all of the adverse physiological symptoms or effects of PCV2 infections are significantly reduced, ameliorated or totally prevented.

In another preferred embodiment, the composition comprises an inactivated or killed Mh and, optionally, one PRRS antigen.

The composition comprises LPS and oil to generate an oil-in-water formulation. As shown in the examples, such particular formulation generates a potent and stable immune response in treated animals. In particular, the composition induces a cellular and humoral immune response, with a proper Th1/Th2 balance suitable to effectively protect animals from the diseases caused by the pathogen.

LPS for use in the present invention is preferably a bacterial LPS, particularly derived from *E. coli*. LPS is commercially available and may be obtained from various sources. It is preferably purified from *E. coli* supernatant, most preferably at Day 5. LPS for use in the invention should be pharmaceutically compatible. Also, it is preferred to use the LPS in an amount between $5 \cdot 10^2$ and $5 \cdot 10^4$ EU/ml, even more preferably between $10^3$ and $10^4$ EU/ml, typically in the amount of about $5 \cdot 10^3$ EU/ml. Alternatively, the LPS is used at 0.1-2.5% v/v in the composition, more preferably below 1% v/v. In a specific example, the LPS is LPSJ5 from *E. coli*.

The oil is typically present in the composition at a final concentration of about 1-50% (v/v) and more typically at a final concentration of about 10-35% (v/v), typically 10%, 15%, 20%, 25%, or 30% (v/v). In a preferred embodiment, the oil is present at a final concentration of between 10-20% (v/v). In a specific embodiment, the oil is present at a concentration of about 15% (v/v).

The results obtained show that, at high oil content (e.g., between 10-25%), the composition induces a strong response even at low antigen dosage.

A preferred composition of the invention is an oil-in-water composition comprising an inactivated or killed bacterium, LPS, and 10-20% (v/v) oil, more preferably 12-18% (v/v) oil.

A further preferred composition of this invention is an oil-in-water composition comprising an inactivated or killed bacterium, at least $5 \cdot 10^2$ EU/ml of LPS, and 10-20% (v/v) oil.

A further preferred composition of this invention is an oil-in-water composition comprising at least $10^3$ inactivated bacteria, at least $5 \cdot 10^2$ EU/ml of LPS, and 10-20% (v/v) oil.

A specific example of a composition of the invention is an oil-in-water composition comprising at least $10^3$ inactivated bacteria, about $5 \cdot 10^3$ EU/ml of LPS, and about 15% (v/v) oil.

In the most preferred embodiment, the bacterium is an inactivated, killed or non-virulent Mh.

The oil in the formulation may be selected from various pharmaceutically compatible oils. They include vegetal oils, mineral oils, animal oils and combinations thereof. Example of vegetal oils include or may be derived from peanut oil, safflower oil, olive oil, cottonseed oil, maize oil, sesame oil, or coconut oil. Examples of mineral oils include or may be derived from light liquid paraffin oil or heavy liquid paraffin oil.

In a preferred embodiment, the oil comprises liquid paraffin oil, more preferably light liquid paraffin oil. In a further preferred embodiment, the oil comprises liquid paraffin oil in admixture with sorbitan trioleate and/or polysorbate 80. The combination may be made according to the following ratios:

| | |
|---|---|
| light liquid paraffin oil | 50-80%, preferably 58-70% v/v |
| sorbitan trioleate | 13-18%, preferably 15-17% v/v |
| polysorbate 80 | 7-32%, preferably 13-25% v/v |

In a particular embodiment, the oil is MixA, with the following composition:

| | |
|---|---|
| light liquid paraffin oil | 60-63% v/v |
| sorbitan trioleate | 15-16% v/v |
| polysorbate 80 | 25-21% v/v |

The composition of the invention may comprise additional ingredients. In particular, in a preferred embodiment, the composition of the invention is a vaccine, and may comprise additional ingredients such as pharmaceutically acceptable carriers, excipients, diluents, freeze-drying stabilizers, wetting or emulsifying agents, pH buffering agents, gelling or viscosity enhancing additives, and preservatives, depending on the route of administration.

Examples of pharmaceutically acceptable carriers, excipients or diluents include, but are not limited to, demineralized or distilled water; saline solution; volatile silicones; squalane; cellulose derivatives such as methylcellulose, ethylcellulose, carboxymethylcellulose, carboxymethylcellulose sodium salt, or hydroxypropyl methylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia; and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Examples of freeze-drying stabilizers may be for example carbohydrates such as sorbitol, mannitol, starch, sucrose, dextran or glucose, proteins such as albumin or casein, and derivatives thereof.

The compositions or vaccines may be liquid formulations such as an aqueous solution, a water-in-oil or oil-in-water emulsion, a syrup, an elixir, a tincture, or a preparation for parenteral, subcutaneous, intradermal, intramuscular or intravenous administration (e.g., injectable administration), such as sterile suspensions or emulsions. Such formulations are known in the art and are typically prepared by dissolution of the antigen and other typical additives in the appropriate carrier or solvent systems. Liquid formulations may also include suspensions and emulsions that contain suspending or emulsifying agents.

The route of administration can be percutaneous, via mucosal administration, or via a parenteral route (intradermal, intramuscular, subcutaneous, intravenous, or intraperitoneal). Vaccines compositions according to the present invention may be administered alone, or can be co-administered or sequentially administered with other treatments or therapies.

The invention also relates to a method for immunizing or inducing an immune response in pigs comprising administering a vaccine as described above, as well as a method of vaccination in pigs, and methods of treating and/or preventing infectious diseases.

The vaccines of the invention can conveniently be administered intranasally, transdermally (i.e., applied on or at the skin surface for systemic absorption), parenterally, ocularly, etc. The parenteral route of administration includes, but is not limited to, intramuscular, intravenous, and intraperitoneal routes and the like.

The dosage of the vaccine made according to the present invention will depend on the species, breed, age, size, vaccination history, and health status of the animal to be vaccinated, as well as of the route of administration, i.e., subcutaneous, intradermal, oral, intramuscular or intravenous administration.

The vaccines of the invention can be administered as a single dose or in repeated doses. The vaccines of the invention can be administered alone, or can be administered simultaneously or sequentially administered with one or more further compositions, such as other porcine immunogenic or vaccine compositions. Where the compositions are administered at different times the administrations may be separate from one another or overlapping in time. Typically, the vaccine is administered in the form of dosages of between 0.5 and 3 ml each.

Vaccines of the invention are particularly suited for treating pigs, adult pigs, and also young pigs, piglets or pregnant females, or other types of non-human mammals. Vaccination of pregnant females confers passive immunity to the newborns via the transmission of maternal antibodies. The pigs may be less than 7, 6, 5, 4, 3, 2 or 1 week old; 1 to 6 weeks old; 2 to 5 weeks old; or 3 to 4 weeks old. For instance, "test" animals may be administered with the vaccine of the invention in order to evaluate the performance of the vaccine with a view to eventual use or development of a vaccine for pigs. Desirably, the vaccine is administered to a subject who has not yet been exposed to the pathogen. Preferably, the subject is a pig which is in need of vaccination against *mycoplasma*, Postweaning Multisystemic Wasting Syndrome (PMWS) and/or Porcine Dermatitis and Nephropathy Syndrome (PDNS).

The present invention provides a container comprising an immunologically effective amount of the vaccine as described above. The invention also provides vaccination kits comprising an optionally sterile container comprising an immunologically effective amount of the vaccine, means for administering the vaccine to pigs, and eventually an instruction manual including information for the administration of the immunologically effective amount of the composition to pigs for treating and/or preventing infectious diseases.

The present invention further relates to a method of generating an antibody which is capable of binding to pathogen or a sub-unit thereof. The method may comprise immunizing an animal, such as a rabbit, guinea pig, or rodent, and harvesting the antibody produced thereby. The antibodies of the invention may be polyclonal or monoclonal antibody preparations, monospecific antisera, human antibodies, or hybrid or chimeric antibodies, such as humanized antibodies, altered antibodies, (Fab')2 fragments, F(ab) fragments, Fc fragments, single-domain antibodies, dimeric or trimeric antibody fragments or constructs, or functional fragments thereof which bind to the antigen in question. Antibodies may be produced using techniques well-known to those of skill in the art and disclosed in A Laboratory Manual, Harlow and Lane, eds., Cold Spring Harbor Laboratory, N.Y. (1988).

The following is provided to illustrate embodiments of the invention and should not be viewed as limiting the scope of the invention.

EXAMPLES

1. Preparation of Vaccine Formulations
Composition of Vaccine

|  | v/v % |
|---|---|
| Aqueous phase (containing *E. coli* J5 LPS adjuvant) | 85 |
| Oil (MixA) | 15 |

Adjuvants

| | Composition | | | Used amount in the |
|---|---|---|---|---|
| Name | Chemical description | v/v % | | vaccine |
| MixA oil | light liquid paraffin oil | 60-63 | | 15 v/v % |
| | sorbitan trioleate | 15-16 | | |
| | polysorbate 80 | 25-21 | | |
| *E. coli* J5 LPS | LPS | | | $5 * 10^3$ EU/mL |

Preparation/Emulsification Method

The emulsification method is a one-step mixing procedure.

All ingredients (surfactants) are mixed into the oil, then the oil phase is added to the aqueous phase containing the needed amount of antigen and *E. coli* J5 LPS adjuvant component under stirring. There is no need for a specific homogenization step.

Start mixing sterilized and room-temperature (20-25° C.) oil adjuvant and mix it for at least 20 minutes.

Start adding oil adjuvant into the aqueous phase through the sterile inlet port while mixing vigorously. Vigorous mixing of the aqueous phase is necessary (280-320 rpm). The speed of the addition has to be max. 4-8 kg/minute.

After the addition, the emulsion is mixed for at least 60 minutes at the same rpm.

Following this method, additional vaccines are prepared with the following formulation:

|  | v/v % |
|---|---|
| Aqueous phase (containing *E. coli* J5 LPS adjuvant) | 90 |
| Oil (MixA) | 10 |
| Aqueous phase (containing *E. coli* J5 LPS adjuvant) | 80 |
| Oil (MixA) | 20 |

2. Preparation of Additional Vaccine Compositions
The following vaccines preparation have been prepared.

TABLE 1

Composition of the vaccines

| | | | Antigen (Mh) | | | | | |
|---|---|---|---|---|---|---|---|---|
| | | | ATP lum./mL | | | | | |
| vaccine | Oil | CCU/mL | Before inact. | After inact. | $OD_{540}$/mL | v/v % | Oil (v/v %) | J5 LPS (v/v %) |
| 1 | MixA | $3 \times 10^8$ | $6.77 \times 10^5$ | 506.1 | 0.150 | 0.60 | 15 | 2 |
| 2 | MixA | $2.81 \times 10^9$ | $6.77 \times 10^5$ | — | 0.087 | 0.51 | 15 | 0.4 |

TABLE 1-continued

Composition of the vaccines

| | | Antigen (Mh) | | | | | |
|---|---|---|---|---|---|---|---|
| | | ATP lum./mL | | | | | |
| vaccine | Oil | CCU/mL | Before inact. | After inact. | $OD_{540}$/mL | v/v % | Oil (v/v %) | J5 LPS (v/v %) |
| 3 | MixA | $2.81 \times 10^9$ | $6.77 \times 10^5$ | — | 0.087 | 0.51 | 10 | 0.4 |
| 4 | MixA | $9.35 \times 10^9$ | $2.26 \times 10^6$ | — | 0.291 | 1.70 | 15 | 0.4 |
| 5 | MixA | $9.35 \times 10^9$ | $2.26 \times 10^6$ | — | 0.291 | 1.70 | 10 | 0.4 |

3. Immune Protection

Immune protection against *Mycoplasma hyopneumoniae* (Mh) infection is mediated by both the humoral and the cellular arms of the immune system, with more emphasis on the latter. Therefore, it is crucial for an efficient Mh vaccine to induce cell-mediated immune (CMI) response in swine in addition to antibody response. Using vaccine formulations of Example 2, we were able to generate a balanced Th1/Th2 immune response in swine upon vaccination with inactivated Mh vaccine.

Materials and Methods

Six groups of 10 four-week-old piglets, seronegative to Mh, were immunized once at 3 weeks of age (D21), with oil-in-water formulations of inactivated Mh antigen plus a non-toxic LPS adjuvant derived from *E. coli* J5 in different dose combinations (Table 2).

TABLE 2

Vaccine formulations applied to 6 piglet groups. The vaccines correspond to the vaccine # in Table 1

| Vaccine | Antigen | Oil | LPS |
|---|---|---|---|
| 1 | low | high | high |
| 2 | low | high | low |
| 3 | low | low | low |
| 4 | high | high | low |
| 5 | high | low | low |
| ctr | — | high | low |

A delayed type hypersensitivity (DTH) test was performed on half of each group on D40 using intradermal injection of purified Mh antigen. Phytohaemagglutinin (PHA) at 20 μg/mL concentration in 0.1 mL was used as positive control. Skin thickness was measured with a pressure-sensitive digital caliper (Mitutoyo, Japan). Blood samples were taken from the second half of each group for interferon-γ (IFNγ) ELISPOT and antibody ELISA on D40. A porcine IFNγ ELISPOT kit (R&D, USA) and an ELISPOT reader (CTL, USA) were used for the quantification of antigen-specific cytokine secretion by in vitro stimulated PBMC.

Briefly, separated PBMC was plated in 96-well PVDF-bottom plates in duplicate at $5 \times 10^5$ cells per well and stimulated with concentrated purified *Mycoplasma hyopneumoniae* antigen. Non-stimulated cells were used as negative controls. PHA-stimulated cells and recombinant porcine IFN-γ served as positive controls. After 72-96 hours incubation at room temperature (RT) cells were washed out and biotinylated anti-pIFN-γ antibody was measured into the wells for an overnight incubation at 4° C. Spot formation was visualized by 2 hours incubation with Streptavidin-AP conjugate at RT followed by 1 hour incubation with BCIP/NBT substrate at RT. Spot numbers per well were analyzed by a CTL ELISPOT analyzer (S5 Versa).

Mh-specific serum antibody titer was determined with an indirect ELISA assay.

Results

FIG. 1 shows the effect of different formulations on the cellular and humoral immune response. Interestingly, higher antigen dose itself did not increase the humoral response while slightly increasing both CMI responses (Group 5 vs. 3). The most balanced Th1/Th2 adjuvant effect was achieved by the high LPS+ high oil combination at low antigen dose (Group 1 vs. 3). In this effect LPS played the major role (Group 1 vs. 2). The effect of oil adjuvant was more pronounced at high antigen dose (Group 4 vs. 5) than at low antigen dose (Group 2 vs. 3).

Conclusions and Discussion

Here, we described the adjuvant effect of different vaccine formulations on cellular immune response and serum antibody titer measured by DTH, IFNγ ELISPOT and quantitative antibody ELISA, respectively. Oil-in-water formulation combined with the non-toxic LPS adjuvant resulted in a balanced Th1/Th2 immune response in seronegative animals. This formulation provides long-lasting CMI and humoral immune memory.

4. Duration of Immunity after One Shot of *Mycoplasma hyopneumoniae* Vaccine in Pigs

*Mycoplasma hyopneumoniae* is the etiological agent of enzootic pneumonia (EP) in swine. The disease is characterized by high morbidity in animals of mid-finishing to slaughter age; nevertheless the circulation of the pathogen usually starts in nursery after mixing of weaned pigs. The severity of clinical signs highly depends on the virulence and infectious dose of *M. hyopneumoniae* (Mh) strain. The aim of this study was to confirm the six months of protection conferred by vaccines of the invention against a heavy challenge.

Material and Methods:

Study design, in total 25 Mh seronegative 3-week-old piglets were divided into 2 separated groups. Twelve piglets of group 1 (G1) received a 1 shot vaccination with vaccine #2 of Table 1, at day 0 (D0). Thirteen non-vaccinated control piglets of the same age were involved in the study in group 2 (G2). Challenge was performed at fattener age, on two consecutive days on D175 and D176. All animals were challenged intranasally with a high dose of Mh. (9 log 10 color changing units/animal). They were observed for respiratory clinical signs for 28 days and then euthanized for necropsy and lung scoring on D204 around 6.5 months of age. Clinical and post-mortem parameters were used for both studies: 1) respiratory symptoms, 2) rectal temperature, 3) body weight, and 4) lung scoring in accordance with European Pharmacopoeia. The affected area of the lobes was expressed in percentage in relation to the whole lobe mass.

Figure 2:
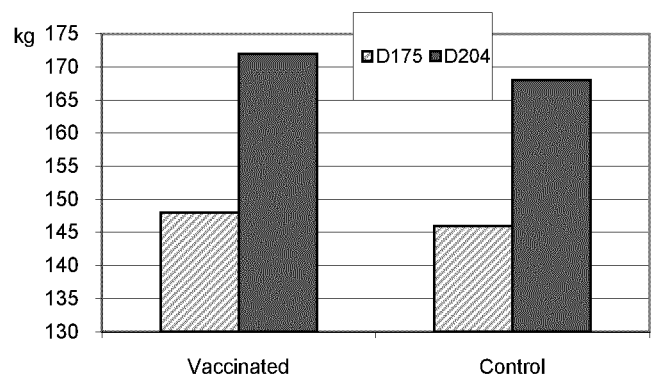
FIG. 2: Body weight comparison of pigs at the time of challenge (D175) and slaughtering (D204).
Figure 3:
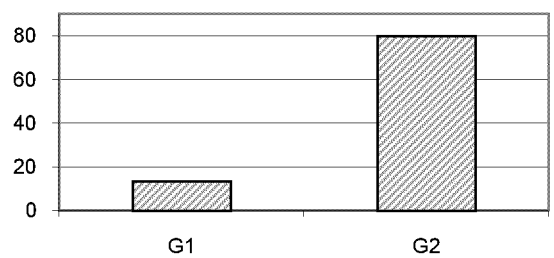
FIG. 3: The means of cumulative lung scores of vaccinated and control animals.

Calculation of the final (or cumulative) lung score values was completed by lung lobe dependent multiplication factor (1).
Results:
1) No EP-specific death occurred in the post-challenge observation period. Neither vaccinates nor the control animals showed respiratory clinical signs. 2) After the challenge no fever occurred either in control (G2) or vaccinated animals (G1). 3) The average body weight of vaccinates was 3.8 kg higher than the controls' (G2) (see FIG. 2). 4) The total lung scores of control animals were 7.75 times higher than those of the vaccinated pigs in G1. The difference was significant in favor of the vaccinated group. (P=0.0015) (see FIG. 3).
Discussion 6 months' duration of protective immunity after vaccination with a composition of the invention was proven by a heavy experimental challenge trial using 1 shot of the vaccine at 3 weeks of age in immunized pigs and non-vaccinated controls. The vaccine prevented the body weight loss due to EP and significantly decreased the severity of pathological changes caused by *Mycoplasma hyopneumoniae* infection.

5. Immunological Status of Vaccinated Animals
5.1. Humoral Immune Response

Table 3 below reports the mean of the antibody titre (EU/ml) before and after vaccination and after challenge

| Groups | D0 | D13 | D63 | D126 | D175 | D202 |
|---|---|---|---|---|---|---|
| Vaccinated | 0.2 | 0.2 | 3.2 | 3.0 | 6.1 | 17.3 |
| Control | 0.1 | 0.1 | 0.7 | 0.2 | 0.1 | 0.1 |

Figure 4:
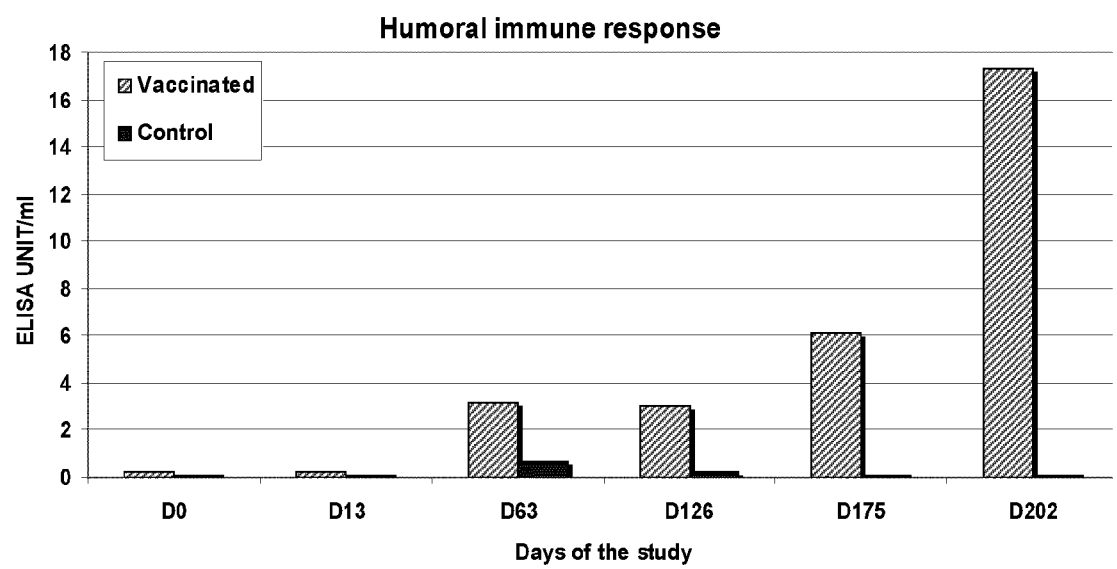
FIG. 4: Humoral immune response of the piglets.

On D63 after vaccination, measurable humoral immune response was detected against *M. hyopneumoniae* in the vaccinated piglets. Four weeks after challenge high antibody levels were detected against *M. hyopneumoniae* in the vaccinated animals. 173 times higher antibody levels developed against *M. hyopneumoniae* in the vaccinated animals than in the control animals at the end of the study (D202) (see FIG. 4).

5.2. Cellular Immune Response

Table 4 below reports the mean of antigen-specific white blood cell number/6 log 10 peripheral blood mononuclear cells (PBMC).

| Day of sampling | Mean of ELISPOT values | |
|---|---|---|
| | Group 1 (vaccinated) | Group 2 (control) |
| D13 | 23.75 | 0.56 |
| D90 | 25.31 | 1.64 |
| D126 | 5.38 | 0.83 |
| D175 | 10.38 | 2.00 |

The results show that 13 days after vaccination (D13) the cellular immune response was already 42.41 times higher in the vaccinated animals compared to the controls. 5.19 times more antigen-specific white blood cells were found in the vaccinated animals than in the controls before the challenge infection (D175).

After statistical analysis, there were significant differences between the mean antigen-specific white blood cell counts of vaccinated and control groups at D13 and D90 ($P_{D13}$=0.027, $P_{D90}$=0.016).

The invention claimed is:

1. A composition comprising an antigen and a lipopolysaccharide (LPS) in an oil-in-water formulation, wherein the lipopolysaccharide comprises LPS J5 from *Escherichia coli*, and wherein the oil-in-water formulation comprises liquid paraffin oil in admixture with sorbitan trioleate and/or polysorbate 80.

2. The composition of claim 1, wherein the antigen is a bacterial antigen.

3. The composition of claim 2, wherein said bacterial antigen is an inactivated or killed bacterium.

4. The composition of claim 2, wherein the bacterial antigen is an inactivated or killed *mycoplasma*.

5. The composition of claim 4, wherein said inactivated or killed *mycoplasma* is an inactivated or killed *Mycoplasma hyopneumoniae*.

6. The composition of claim 1, wherein said composition comprises several distinct antigens.

7. The composition of claim 5, wherein said composition comprises an inactivated or killed *Mycoplasma hyopneumoniae* and at least one PCV2 or PRRS antigen.

8. The composition of claim 1, wherein the oil-in-water formulation comprises from 1 to 30% (v/v) oil, from 5 to 30% (v/v) oil, from 10-30% (v/v) oil, from 10-25% (v/v) oil or 10-20% (v/v) oil.

9. The composition of claim 1, wherein the oil comprises liquid paraffin oil in admixture with sorbitan trioleate and polysorbate 80.

10. The composition of claim 1, wherein said composition comprises an inactivated or killed bacterium, at least $5\times10^2$ EU/ml of LPS, and 10-20% (v/v) oil.

11. The composition of claim 10, wherein said composition comprises at least $10^3$ EU/ml of LPS.

12. A method of stimulating an immune response in a non-human animal against a pathogen, comprising administering to the animal a composition comprising a composition according to claim 1 to said non-human animal, said antigen being an antigen from a pathogen.

13. A method for inducing or stimulating an immune response in a non-human animal against a bacterial antigen comprising administering a composition according to claim 1 to said non-human animal.

14. A method for stimulating an immune response in pigs or piglets against *Mycoplasma hyopneumoniae* (Mh), comprising administering to said pigs or piglets a composition according to claim 5.

15. The method according to claim 14, wherein said composition is administered to piglets.

* * * * *